United States Patent
Finkelstein et al.

(10) Patent No.: US 10,444,239 B2
(45) Date of Patent: Oct. 15, 2019

(54) METHODS FOR MEASURING CARCINOEMBRYONIC ANTIGEN

(71) Applicant: Interpace Diagnostics Corporation, Parsippany, NJ (US)

(72) Inventors: Sydney David Finkelstein, Pittsburgh, PA (US); Sara Ann Jackson, Pittsburgh, PA (US); Jamie Michelle Bleicher, Butler, PA (US); Eric Matthew Gayle Ellsworth, Pittsburgh, PA (US); Dennis Morgan Smith, Jr., St. Augustine, FL (US)

(73) Assignee: INTERPACE DIAGNOSTICS CORPORATION, Parsippany, NJ (US)

( * ) Notice: Subject to any disclaimer, the term of this patent is extended or adjusted under 35 U.S.C. 154(b) by 0 days.

(21) Appl. No.: 15/147,960

(22) Filed: May 6, 2016

(65) Prior Publication Data

US 2017/0089907 A1  Mar. 30, 2017

Related U.S. Application Data

(63) Continuation of application No. 14/092,036, filed on Nov. 27, 2013, now Pat. No. 9,341,628.

(60) Provisional application No. 61/731,725, filed on Nov. 30, 2012, provisional application No. 61/824,623, filed on May 17, 2013, provisional application No. 61/840,963, filed on Jun. 28, 2013.

(51) Int. Cl.
*G01N 33/50* (2006.01)
*G01N 33/574* (2006.01)

(52) U.S. Cl.
CPC .............................. *G01N 33/57473* (2013.01)

(58) Field of Classification Search
None
See application file for complete search history.

(56) References Cited

U.S. PATENT DOCUMENTS

| | | | |
|---|---|---|---|
| 5,188,964 A | 2/1993 | McGuire et al. | |
| 5,320,840 A | 6/1994 | Camble et al. | |
| 5,380,645 A | 1/1995 | Vogelstein | |
| 5,491,062 A | 2/1996 | McKenzie et al. | |
| 5,580,728 A | 12/1996 | Perlin | |
| 5,670,325 A | 9/1997 | Lapidus et al. | |
| 5,830,711 A | 11/1998 | Barany et al. | |
| 5,843,644 A | 12/1998 | Liotta et al. | |
| 6,143,529 A | 11/2000 | Lapidus et al. | |
| 6,300,077 B1 | 10/2001 | Shuber et al. | |
| 6,340,563 B1 | 1/2002 | Finkelstein et al. | |
| 6,428,964 B1 | 8/2002 | Shuber | |
| 6,465,177 B1 | 10/2002 | Hoon | |
| 6,750,020 B2 | 6/2004 | Shuber | |
| 6,919,174 B1 | 7/2005 | Shuber | |
| 7,014,999 B2 | 3/2006 | Finkelstein et al. | |
| 2001/0034038 A1 | 10/2001 | Hung | |
| 2003/0165895 A1 | 9/2003 | Czemiak et al. | |
| 2006/0088871 A1 | 4/2006 | Finkelstein et al. | |
| 2006/0115844 A1 | 6/2006 | Finkelstein et al. | |
| 2006/0141497 A1 | 6/2006 | Finkelstein et al. | |
| 2006/0154274 A1 | 7/2006 | Finkelstein et al. | |
| 2011/0008914 A1 | 1/2011 | Yeung et al. | |

FOREIGN PATENT DOCUMENTS

| | | |
|---|---|---|
| EP | 0671473 A1 | 9/1995 |
| WO | 9419492 A1 | 9/1994 |
| WO | 199854364 A1 | 12/1998 |
| WO | 199910528 A1 | 3/1999 |
| WO | 02086448 A2 | 10/2002 |
| WO | 2006047481 A2 | 5/2006 |

OTHER PUBLICATIONS

Pitman et al. (Cancer Cytopathology, p. 1-13, Feb. 25, 2010).*
Boot et al., "Validity of carcinoembryonic antigen and carbohydrate antigen 19-9 measurements in pancreatic cyst fluid with a serum-based immunoassay,"Clinical Chemistry (2010) 56(8):1351-1352.
Brugge et al., "Diagnosis of pancreatic cystic neoplasms: a report of the cooperative pancreatic cyst study," (2004) 126(5):1330-1336.
Khalid et al., "ACG practice guidelines for the diagnosis and management of neoplastic pancreatic cysts," Am J Gastroenterol (2007) 102(10):2339-2349.
http://www.salimetrics.com/assets/documents/Spit.sub.—Tips.sub.—.sub.—Inter.sub.—Intra.sub.—Assay.sub.—Coefficients.sub.—of.sub.—Variabilit-y.pdf.
Reineke M. et al., "'p53 mutations in human adrenocortical neoplasms: immunohistochemical and molecular studies.'," J. Clin Endocrinol. and Metab. (1994), vol. 78 (No. 3), p. 790-794, Endocrine Society, Chevy Chase, Maryland.
Kôsel et al., "Use of neuropathological tissue for molecular genetic studies: parameters affecting DNA extraction and polymerase chain reaction," Acta Neuropathol. (1994) 88, pp. 19-25, Springer Verlag, Berlin, Germany.
An, et al., "Removal of inhibitor(s) of the polymerase chain reaction from formalin fixed, paraffin wax embedded issues," Journal of Clinical Pathology 1991, 44 pp. 924-927, BMJ Pub. Group, London, United Kingdom.

(Continued)

*Primary Examiner* — Nelson B Moseley, II
(74) *Attorney, Agent, or Firm* — Pepper Hamilton LLP

(57) ABSTRACT

Disclosed herein are methods of accurately measuring carcinoembryonic antigen in a biological sample and methods of identifying and treating a mucinous cyst in a subject.

10 Claims, 8 Drawing Sheets

(56) References Cited

OTHER PUBLICATIONS

Sen et al., "Microdissected Double-Minute DNA Detects Variable Patterns of Chromosomal Localizations and Multiple Abundantly Expressed Transcripts in Normal and Leukemic Cells," Genomics, 19(3), pp. 542-551 (1994) Academic Press, Inc., San Diego, California.

Shibata et al. "Specific Genetic Analysis of microscopic tissue after selective ultraviolet radiation fraction and the PCR", Am. J. of Pathology, vol. 121, No. 3, pp. 539-543, Sep. 1992, The American Society for Investigative Pathology, Bethesda, Maryland.

Slebos, RJC, et al., "'K-ras oncogene activation as a prognostic marker in adenocarcinoma of the lung.'," New Engl. J. Med. ( 1990), vol. 323 (No. 9), p. 561-565, Massachusetts Medical Society, Boston, Massachusetts.

Stenersen et al., "The selection of thin epithelial layers: a method for single cell preparations of very small biopsies from the vocal cords," Analytical Cellular Pathology, 2, pp. 253-258, (1990) Elsevier Science Publishers B.V., Amsterdam, Holland.

Goelz, et al., "Purification of DNA from Formaldehyde Fixed and Paraffin Embedded Human Tissue," Biochemical and Biophysical Research Communications, vol. 130, No. 1, 1985, pp. 118-126, Academic Press, New York, New York.

Murase M.D., et al., "Influence of Histochemical and Immunohistochemical Stains on Polymerase Chain Reaction," Modern Pathology, an official journal of the United States and Canadian Academy of Pathology, Inc., vol. 13, No. 2, po. 14 7-151 (2000), Williams & Wilkins, Baltimore, Maryland.

Talmadge, "The pharmaceutics and delivery of therapeutic polypeptides and proteins," Advanced Drug Delivery Reviews, 10, pp. 247-299 (1993) Elsevier Science Publishers B.V., Amsterdam, Holland.

Teramoto et al. "Application of PCR to the microscopically identified cells on the slides" Acta Med. Okayama, vol. 48, No. 4, pp. 189-193, 1994, Okayama University Medical School, Okayama, Japan.

Lamballerie, et al., "Improved current methods for amplification of DNA from routinely processed liver tissue by PCR," Journal of Clinical Pathology 1994, 47, pp. 466-467, BMJ Pub. Group, London, United Kingdom.

Khalid A et al., "Free floating DNA mutational allelotyping ofEUS guided aspirates of pancreatic cysts is predictive of inderlying biological behavior: Preliminary data on a novel techniquec." Pancreas, vol. 27, No. 4, Nov. 2003, p. 391, The American Pancreatic Association; Chicago, Illinois.

Khalid A et al., "Mutational Allelotyping of Aspirated Free-Floating DNA Predicts the Biological Behavior of Cystic Pancreatic Neoplasms" Gastrointestinal Endoscopy, vol. 59, No. 5, Apr. 2004, Elsevier, Netherlands.

Hruban RH et al., "genetic progression in the pancreatic ducts." The American Journal of Pathology, vol. 156, No. 6, Jun. 2000, pp. 1821-1825, The American Society for Investigative Pathology, Bethesda, Maryland.

Khalid A et al., "Molecular diagnosis of solid and cystic lesions of the pancreas" Gastroenterology Clinics of North America, vol. 33, No. 4, 2004, p. 891-906, W.B. Saunders Co., Philadelphia, Pennsylvania.

Khalid A et al., "The Role of Pancreatic Cyst Fluid Molecular Analysis in Predicting Cyst Pathology" Clinical Gastroenterology and Hepatology, vol. 3, No. 10, p. 967-973, Oct. 2005, American Gastroenterological Association, Philadelphia, Pennsylvania.

Khalid A et al., "First hit K-ras point mutation followed by tumor suppressor gene allelic loss predicts malignancy in EUS guided pancreatic cyst aspirate." Pancreas, vol. 29, No. 4, Nov. 2004 p. 357, Annual Meeting of the American Pancreatic Association; Chicago, Illiniois.

Khalid A et al., "Comparison of EUS guided pancreatic Cyst (PC) Aspirate Cea, DNA Quantity and Quality: Mutational Acquisition Pattern in Predicting Malignancy." Gastrointestinal Endoscopy, vol. 61, No. 5, Apr. 2005. Elsevier, Netherlands.

Isaacs et al., "Detection of LOH and mitochondrial DNA alterations in ductal lavage and nipple aspirate fluids from high-risk patients," Breast Cancer Research and Treatment, vol. 84, No. 2, Mar. 2004, pp. 99-105.

Liloglou Triantafillos et al., "Cancer-specific Genomic Instability in Bronchial Lavage: A Molecular Tool for Lung Cancer Detection," Cancer Research, vol. 61, No. 4, Feb. 15, 2001, DD. 1624-1628.

Pricolo et al., "Prognostic Value of TP53 and K-ras-2 Mutational Analysis in Stage III Carcinoma of the Colon," American Journal of Surgery, vol. 171, No. 1, Jan. 1996, pp. 41-46.

Minamoto et al., "K-ras Mutation: Early Detection in Molecular Diagnosis and Risk Assessment of Colorectal, Pancreas, and Lung Cancers—A Review," Cancer Detection and Prevention, vol. 24, No. I, 2000, DD. I-.

Evron et al., "Detection of breast cancer cells in ductal lavage fluid by methylatiorrspecific PCR," The Lancet, vol. 357, No. 9265, Apr. 28, 2001, pp. 1335-1336.

Sasatomi et al., "Comparison of Accumulated Allele Loss between Primary Tumor and Lymph Node Metastasis in Stage II Non-small Cell Lung Carcinoma: Implications for the Timing of Lymph Node Metastasis and Prognostic Value," Cancer Research, vol. 62, No. 9, May 1, 2002, DD. 2681-2689.

NonFinal Office Action dated Apr. 1, 2008, in U.S. Appl. No. 11/256,150.

Official Action dated Dec. 18, 2007 by the European Patent Office in European Application No. 05818189.2.

Leob "A Mutator Phenotyp in Cancer", Cancer Research (2001) 61,3230-3239.

Heng et al., "Cancer progression by non-clonal chromosome aberrations." Jornal of Cellular Biochemistry (2006) 98:1424-1435.

Grizzi et al., "Cancer: looking for simplicity and finding complexity." Cancer Cell International (2006) 6:4 pp. 1-7.

Glazier "An Inconvenient Truth: Cancer is a hugely diverse, complex, unpredictable, non-linear, stochastic evolutionary w process." retrieved Sep. 16, 2009 from http://www. cu re can cerp ro ject.o rg/beta/pdf I An %201 n co nve n ient%20T ruth, %20Ca nee r%20 is%20a %20 huge ly%20d ive rse%20co mplex%20stochastic% 20evolutionary%20process.pdf (2009).

Sieben et al. "PCR Artifacts in LOH and MSI Analysis of Microdissected Tumor Cells" Jan. 2000, Human Pathology, 31: 1414-1419.

Skotheim et al. "Evaluation of Loss of Heterozygosity/ Allelic Imbalance Scoring in Tumor DNA" May 2001, Cancer Genetics and Cytogenetics, 127(1):64-70.

Bluteau et al. "Semi-automated Quantitative Method for Detecting the Loss of Heterozygosity at Chromosome 4 in Hepatocellular Carcinoma" Nov. 1999, Biosis.

Anderson et al. Intrachromosomal Genomic Instability in Human Sporadic Colorectal Cancer Measured by Genome-Wide Allelotyping and Inter-(Simple Sequence Repeat) PCR, Nov. 2001, Cancer Research 61(22):8274-8283.

Gall et al., "DNA Amplification by polymerase chain reaction from brain tissues embedded in paraffin," Int. J. Exp. Path. (1993) 74, DD 333-397.

Hodges et al., "Expanded TcR Vb5 1 family in a high-grade B cell immunoblastic lymphoma," Leukimia (1995), vol. 9, pp. 1108-1112, Nature Publishing Group, London, England.

Saiki, "Chapter I, The Design and Optimization of the PCR," PCR Technology. Principles and applications for DNA amplification, New York, Stockton Press, 1989, DD 7-16.

Hodges et al., "Modification of IgH PCR clonal analysis by the addition of sucrose and cresol red directly to PCR reaction mixes," Clinical Pathology: Molecular Pathology, 1997; vol. 50, pp. 164-166, Molecular Immunology Group, Southampton, UK.

Dixon et al., "Expression profiling of single cells using 3 prime end amplification (TPEA) PCR," Nucleic Acids Research, 1998, vol. 26, No. 19, PD 4426-4431, Oxford University Press, Oxford, England.

Warren et al., "Drad21, a Drosophila rad2 I homologue expressed in S-phase cells," Gene 250 (2000) p. 77-84, Elsevier, London England.

(56) References Cited

OTHER PUBLICATIONS

Husain, "Complex expression of natural killer receptor genes in single natural killer cells," Immunology 2002, vol. 106, DD 373-380, Blackwell Science Ltd., Oxford, England.

Wistuba et al., "Sequential molecular abnormalities are involved in the multistage development of squamous cell lung carcinoma," Oncogene (1999), vol. 18, pp. 643-650, Nature Publishing Group, [Basingstoke, England.

Wistuba et al., "Allelic Losses at Chromosome 8p2 I-23 are Early and Frequent Events in the Pathogenesis of Cancer," Cancer Research, vol. 59, (1999), pp. 1973-1979, American Association for Cancer IResearch, Baltimore, MD.

Daido, S. et al., "Loss of heterozygosity on chromosome IOq associated with malignancy ad prognosis in astrocytic tumors, and discovery of novel loss regions," Oncology Reports (2004), vol. 12, pp. 789-795, National Hellenic Research Foundation, Athens, Greece.

Ohtsu et al., "Clinical Investigation of Neuroblastoma with Partial Deletion in the Short Arm of Chromosome I," Clinical Cancer Research, vol. 3, pp. 1221-1228, Jul. 1997.

Loupart et al., "Allelic Imbalance on Chromosome I in Human Breast Cancer. I. Minisatellite and RFLP Analysis," Genes, Chromosomes & Cancer, (1995) vol. 12, pp. 16-23, Wiley-Liss, Inc., New York, New York.

Yeh et al., "Frequent Genetic Alterations at the Distal Region of Chromosome Ip in Human Hepatocelular Carcinomas," Cancer Research, vol. 54, pp. 4188-4192, Aug. 1, 1994, American Association for Cancer Research, Baltimore, MD.

Thompson et al., "Loss of Heterozygosity in Chromosome 14q in Neuroblastoma," Medical and Pediatric Oncology, vol. 36, DP 28-31 (2001) Wiley-Liss, Inc., New York, New York.

Hung, "Allele-Specific Chromosome 3p Deletions Occur at an Early Stage in the Pathogenesis of Lung Carcinoma," JAMA 1995, vol. 273, pp. 558-563, American Medical Association, Chicago, IL.

Husman et al., "Processing of long-stored archival cervical smears for human papillomavirus detection by the polymerase chain reaction," British Journal of Cancer ( 1995) 72, pp. 412-417 University College London, London, United Kingdom.

Ben-Ezra et al., "Effect of Fixation on the Amplification of Nucleic Acids from Paraffin-embedded Material by the polymerase Chain Reaction," The Journal of Histochemistry and Cytochemistry, 39(3), pp. 351-354 ( 1991) The Histochemical Society, Inc., Seattle, Washington.

Rogers, et al., "Analysis of DNA in Fresh and Fixed Tissue by the Polymerase Chain Reaction," American Journal of Pathology, vol., 136, No. 3, Mar. 1990, pp. 541-548, The American Society for Investigative Pathology, Bethesda, Maryland.

De Giorgi et al., "Formalin-induced infidelity in PCR-amplified DNA fragments," Molecular and Cellular Probes (1994) 8, pp. 459-462, Reed Elsevier Group, London, United Kingdom.

Williams, et al., "A High Frequency of Sequence Alterations is Due to Formalin Fixation of Archival Specimens," American Journal of Pathology, vol. 155, No. 5, (Nov. 1999), pp. 1467-1471, The American Society for Investigative Pathology, Bethesda, Maryland.

Wong, et al., "Mutations in BRCAI from Fixed, Paraffin-Embedded Tissue Can Be Artifacts of Preservation," Cancer Genet. Cytogenet. I 07, pp. 21-27 ( 1998), Reed Elsevier Group, London, United Kingdom.

Miller, et al., "Assessing Allelic Dropout and Genotype Reliability Using Maximum Likelihood," Genetics 160, (Jan. 2002), pp. 357-366, Genetics Society of America, Bethesda, Maryland.

Finkelstein SD, et al., "'Genotypic classification of colorectal adenocarcinoma. Biologica behavior correlates with K-ras-2 mutation type.'," Cancer (1993), vol. 71 (No. 12), p. 3827-3838, American Cancer Society, Atlanta, Georgia.

Finkelstein et al., "'Kras-2 topographic genotyping of pancreatic adenocarcinoma.'," Arch. Surg., vol. 129 (No. 4), p. 367-372, (Apr. 1, 1994), The American Medical Association, Chicago, Illinois.

Florell M.D., "Preservation of RNA for Funcational Genomic Studies: a Multidisciplinary Tumor Bank Protocol," The United States and Canadian Academy of Pathology, Inc., vol. 14, No. 2, pp. 116-128 (2001), Augusta, Georgia.

Tully, et al., "Analysis of 6 VNTR loci by 'multiplex' PCR and automated fluorescent detection," Human Genetics (1993) 92, pp. 554-562, Springer Berlin Heidelberg, Germany.

Gura "Antisense Has Growing Pains," Science, 270, pp. 575-577, (1995) Amer. Assn. For the Advancement of Science, Washington, D.C.

Innis et al. PCR Protocols. Adademic Press, Inc. pp. 3-12, 153-158, 348-355, 1990, Reed Elsevier Group, London, United Kingdom.

Rae, et al., "Genotyping for polymorphic drug metabolizing enzymes from paraffin-embedded and immunohistochemically stained tumor samples," Pharmacogenetics 2003, vol. 13, No. 8, pp. 501-507, Chapman & Hall, London, United Kingdom.

Gillespie, et al., "Evaluation of Non-Formalin Tissue Fixation for Molecular Profiling Studies," American Journal of Pathology, vol. 160, No. 2, (Feb. 2002), pp. 449-457, American Society for Investigative Pathology, Bethesda, Maryland.

Bernstein et al., "Comparison of Techniques for the Successful Detection of BRCAI Mutations in Fixed Paraffin-Embedded Tissue," Cancer Epidemiology, Biomarkers and Prevention, vol. 11, (Sep. 2002), pp. 809-811, American Association for Cancer Research, Philadelphia, Pennsylvania.

Dressen, et al., "Allelic Dropout Caused by Allele-Specific Amplification Failure in Single-Cell PCR of the Cystic Fibrosis .DELTA. F508 Delection," Journal of Assisted Reproduction and Genetics, vol. 13, No. 2, 1996, pp. 112-114, Kluwer Academic/Plenum Publishers, New York, New York.

Forsthoefel, M.D., et al., "Optimization of DNA Extraction from Formalin-Fixed Tissue and Its Clinical Application in Duchenne Muscular Dystrophy," Anatomic Pathology, A.J.C.P, Jul. 1992, pp. 98-104, AASCP Press, Chicago, Illinois.

Küppers et al. "Tracing B cell development in human germinal centres by molecular analysis of single cells picked from histological sections", EMBO J. vol. 12, No. 13, pp. 4955-4967, 1993, Oxford University Press, Oxford, England.

Dressler, et al., "Policy guidelines for the utilization of formalin-fixed, paraffin-embedded tissue sections: the UNC SPORE experience," Breast Cancer Research and Treatment 58, pp. 31-39 (1999), Kluwer Academic Publishers, Netherlands.

Burton, et al., "Comparisoon of Histologic Stains for Use in PCR Analysis of Microdissected, Paraffin—Embedded Tissues," BioTechniques, vol. 24, No. I, pp. 86-91 (1998), Eaton Pub. Co., Natick, Massachusetts.

Meltzer et al. Reduction to homozygosity involving p53 in esophageal cancers demonstrated by PCR. PNAS, vol. 88, pp. 4976-4980, Jun. 1991, National Academy of Sciences, Washington, D.C.

Orkin et al., Report and Recommendations of the Panel to Assess the NIH Investment in Research on Gene Therapy ( 1995), NIH, Bethesda, Maryland.

Oud et al., "Extraction of Nuclei From Selected Regions in Paraffin-Embedded Tissue.sup.1,2," Cytometry, 7, pp. 595-600 (1986) Alan R. Liss, Inc., New York, New York.

Wiegand, et al., "DNA degradation in formalin fixed tissues," Pathologe, Nov. 1996; 17(6); 451-7, Springer- Verlag., Berlin, Germany (abstract in English).

Coates, et al., "Simplified procedures for applying the polymerase chain reaction to routinely fixed paraffin wax sections," Journal of Clinical Pathology 1991, 44, pp. 115-118, BMJ Pub. Group, London, United Kingdom.

Pretlow et al. "K-ras mutation in putative preneoplastic lesions in human colon". J. of Natl. Cancer Institute, vol. 85, No. 24, pp. 2004-2007, Dec. 1993, NIH, Bethesda, Maryland.

\* cited by examiner

METHODS FOR MEASURING CARCINOEMBRYONIC ANTIGEN

CROSS-REFERENCE TO RELATED APPLICATIONS

This application is a continuation of U.S. patent application Ser. No. 14/092,036 filed Nov. 27, 2013, which claims the benefit of U.S. Provisional Application No. 61/731,725 entitled "Methods for measuring carcinoembryonic antigen" filed Nov. 30, 2012, U.S. Provisional Application No. 61/824,623 entitled "Methods for measuring carcinoembryonic antigen" filed May 17, 2013, and U.S. Provisional Application No. 61/840,963 entitled "Methods for measuring carcinoembryonic antigen" filed Jun. 28, 2013, each of which are hereby incorporated herein by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

BRIEF SUMMARY OF THE INVENTION

Embodiments herein are directed to methods of accurately measuring carcinoembryonic antigen in a biological sample, the method comprising: diluting the biological sample with a diluent to form a diluted sample when an amylase level in the biological sample is less than a pre-determined amylase threshold between about 10,000 and about 20,000 units; wherein diluting the biological sample with a diluent comprises diluting the biological sample in a ratio of biological sample to diluent between about 1:10 and about 1:50; and measuring carcinoembryonic antigen in the diluted sample.

Some embodiments further comprise measuring amylase levels in a biological sample. In some embodiments, the biological sample is undiluted. In some embodiments, the diluent is saline, Diluent Universal, or a combination thereof. In some embodiments, the biological sample is selected from pancreatic fluid, pancreatic cyst fluid and combinations thereof. In some embodiments, the pre-determined amylase threshold is about 10,000 units, about 15,000 units, or about 20,000 units.

In some embodiments, diluting the biological sample with a diluent comprises diluting the biological sample with a diluent in a ratio of biological sample to diluent of about 1:40. In some embodiments, diluting the biological sample with a diluent comprises diluting the biological sample with diluent in a ratio of biological sample to diluent of about 1:10.

In some embodiments, the biological sample is not present in sufficient volume to accurately measure carcinoembryonic antigen levels. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels.

In some embodiments, the presence of carcinoembryonic antigen above a predetermined carcinoembryonic antigen threshold in the diluted sample is indicative of a pathological condition. In some embodiments, the carcinoembryonic antigen level threshold is about 192 ng/ml, or about 400 ng/ml. In some embodiments, the pathological condition is selected from a neoplastic condition, a non-neoplastic condition and a combination thereof. In some embodiments, the neoplastic condition is selected from colorectal carcinoma, gastric carcinoma, pancreatic carcinoma, cholangiocarcinoma, intraductal papillary mucinous neoplasm (IPMN), lung carcinoma, breast carcinoma, medullary thyroid carcinoma, mucinous cystic neoplasm, and combinations thereof. In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

Some embodiments are directed to methods of accurately measuring carcinoembryonic antigen in a biological sample, the method comprising: diluting the biological sample with a diluent at a ratio of biological sample to diluent of about 1:10 to about 1:50 to form a diluted biological sample, wherein the amylase level in the biological sample is greater than a pre-determined amylase threshold between about 10,000 and about 20,000 units; measuring carcinoembryonic antigen level in the diluted biological sample; multiplying the carcinoembryonic antigen level by a correction factor to obtain a corrected carcinoembryonic antigen level.

Some embodiments further comprise measuring amylase levels in a biological sample. In some embodiments, the diluent is saline, Diluent Universal, or a combination thereof. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with a diluent comprises diluting the biological sample in a ratio of biological sample to saline of about 1:10. In some embodiments, diluting the biological sample with a diluent comprises diluting the biological sample in a ratio of biological sample to diluent of about 1:40. In some embodiments, the correction factor is about 0.7.

In some embodiments, the biological sample is not present in sufficient volume to accurately measure carcinoembryonic antigen level. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen level.

In some embodiments, a corrected carcinoembryonic antigen level above a predetermined carcinoembryonic antigen threshold is indicative of a pathological condition. In some embodiments, the carcinoembryonic antigen level threshold is about 192 ng/ml, or about 400 ng/ml. In some embodiments, the pathological condition is selected from a neoplastic condition, a non-neoplastic condition and a combination thereof. In some embodiments, the neoplastic condition is selected from colorectal carcinoma, gastric carcinoma, cholangiocarcinoma, pancreatic carcinoma, intraductal papillary mucinous neoplasm (IPMN), lung carcinoma, breast carcinoma, medullary thyroid carcinoma, mucinous cystic neoplasm, and combinations thereof. In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

Some embodiments are directed to methods of identifying a mucinous cyst in a subject, the method comprising: diluting the biological sample with a diluent when an amylase level in the biological sample is less than a pre-determined amylase threshold between about 10,000 and about 20,000 units, to form a diluted sample, wherein diluting the biological sample with a diluent comprises diluting the biological sample in a ratio of biological sample to diluent between about 1:10 and about 1:50; and measuring carcinoembryonic antigen level in the diluted sample; wherein a carcinoembryonic antigen level above a predetermined carcinoembryonic antigen level threshold in the diluted sample is indicative of a mucinous cyst.

Some embodiments further comprise obtaining a biological sample from the subject. In some embodiments, the diluent is saline, Diluent Universal, or a combination thereof. In some embodiments, the biological sample is selected from pancreatic fluid, pancreatic cyst fluid and combinations thereof. Some embodiments further comprise measuring amylase levels in a biological sample. In some embodiments, the biological sample is undiluted.

In some embodiments, the pre-determined amylase threshold is about 10,000 units, about 15,000 units, or about 20,000 units. In some embodiments, diluting the biological sample with a diluent comprises diluting the biological sample in a ratio of biological sample to diluent of about 1:40. In some embodiments, diluting the biological sample with a diluent comprises diluting the biological sample in a ratio of biological sample to diluent of about 1:10.

In some embodiments, the biological sample is not present in sufficient volume to accurately measure carcinoembryonic antigen levels. In some embodiments, the biological sample has a high viscosity. In some embodiments, the high viscosity is due to the presence of mucin in the neat biological sample. In some embodiments, the carcinoembryonic antigen levels in the biological sample exceed the measurement capabilities of an instrument being used to measure carcinoembryonic antigen.

In some embodiments, the carcinoembryonic antigen level threshold is about 192 ng/ml, or about 400 ng/ml.

Some embodiments are directed to methods of identifying a mucinous cyst in a subject, the method comprising: diluting the biological sample with a diluent at a ratio of biological sample to diluent of about 1:10 to about 1:50 to form a diluted biological sample, wherein the amylase levels in the biological sample are greater than a pre-determined amylase threshold between about 10,000 and about 20,000 units; measuring carcinoembryonic antigen level in the diluted biological sample; multiplying the carcinoembryonic antigen level of the diluted biological sample by a correction factor to obtain a corrected carcinoembryonic antigen level, wherein the carcinoembryonic antigen level in the diluted biological sample is less than the carcinoembryonic antigen levels in an aliquot of the same biological sample diluted with diluent in a ratio of biological sample to diluent of about 1:10; and wherein a corrected carcinoembryonic antigen level of above a predetermined carcinoembryonic antigen threshold is indicative of a mucinous cyst.

Some embodiments further comprise obtaining a biological sample from the subject. In some embodiments, the diluent is saline, Diluent Universal, or a combination thereof. Some embodiments further comprise measuring amylase levels in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with a diluent comprises diluting the biological sample in a ratio of biological sample to diluent of about 1:10. In some embodiments, diluting the biological sample with diluent comprises diluting the biological sample in a ratio of biological sample to diluent of about 1:40. In some embodiments, the correction factor is about 0.7. In some embodiments, the carcinoembryonic antigen level threshold is about 192 ng/ml or about 400 ng/ml.

In some embodiments, the biological sample is not present in sufficient volume to accurately measure carcinoembryonic antigen. In some embodiments, the biological sample has a high viscosity. In some embodiments, the high viscosity is due to the presence of mucin in the neat biological sample. In some embodiments, the carcinoembryonic antigen levels in the biological sample exceed the measurement capabilities of an instrument being used to measure carcinoembryonic antigen.

DETAILED DESCRIPTION

Figure 1:
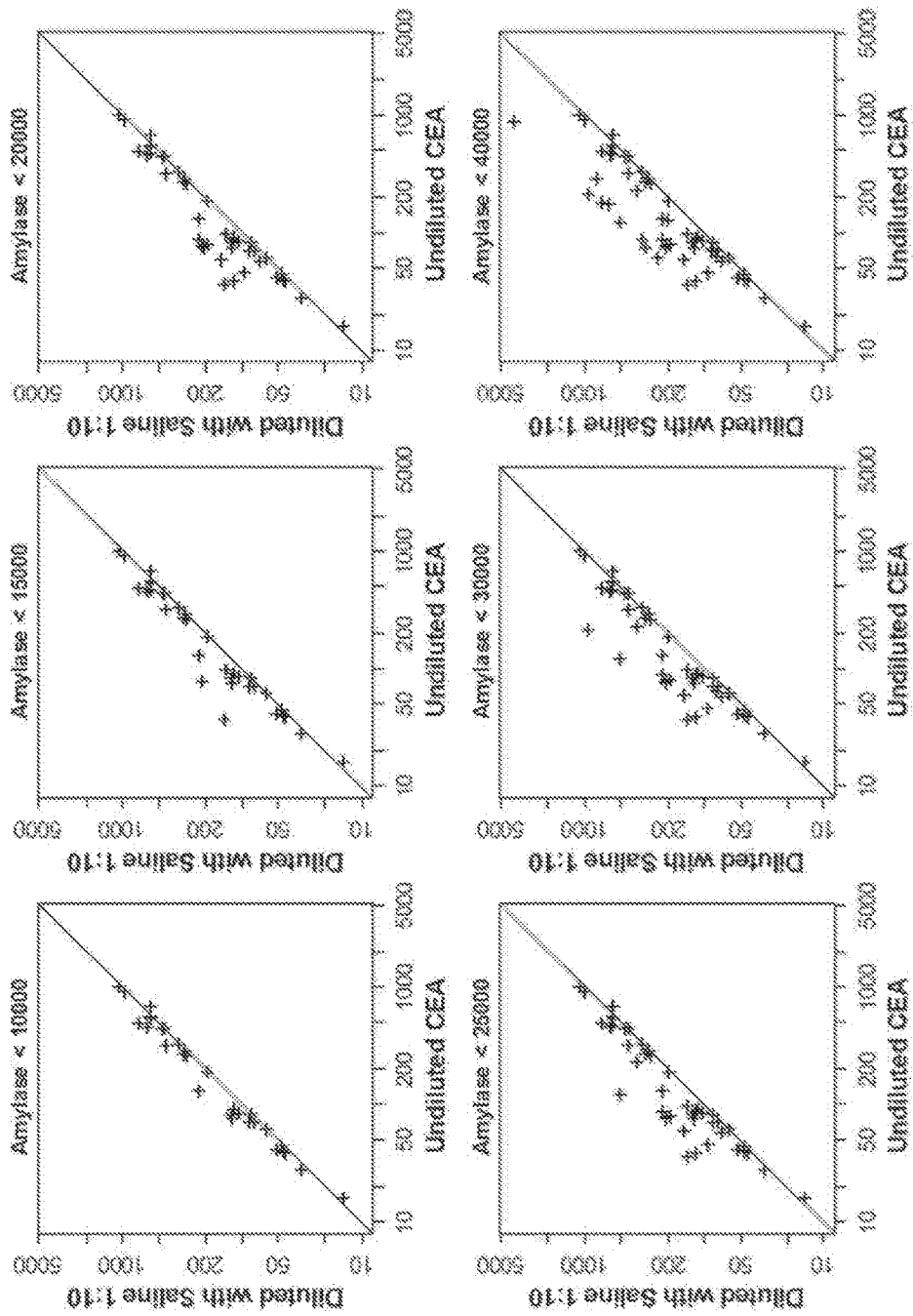
FIG. 1 shows neat carcinoembryonic antigen (CEA) levels in pancreatic cyst fluid samples plotted against CEA levels in pancreatic cyst fluid samples diluted with saline at a ratio of sample to saline of 1:10. Samples are plotted based on amylase levels (e.g. less than 10,000, 15,000, 20,000, 25,000, 30,000 or 40,000)

Imaging techniques, cytology, and biochemical analysis including carcinoembryonic antigen (CEA) concentrations of pancreatic cyst fluid obtained by endoscopic ultrasound-guided fine needle aspiration are used to differentiate pancreatic cyst lesions, particularly those with malignant potential. The American College of Gastroenterology guidelines have outlined the published data relating to the diagnostic performance of pancreatic cyst fluid CEA and concluded that cyst fluid CEA is the single most important factor in determining pancreatic cyst etiology.

In practice, more than 60% of pancreatic cyst and duct fluid CEA testing requires preliminary sample dilution due to i) low aspirated fluid volume, ii) high sample viscosity, and/or iii) initial elevated CEA beyond instrument measurable range (IMR). There are concerns over the fact that CEA measurements in cyst fluid diluted with aqueous salt solutions or water do not accurately reflect the original, undiluted cyst fluid measurement. Disclosed herein are novel methods that provide a more accurate measurement of CEA in diluted pancreatic cyst fluid.

Methods of Accurately Measuring Carcinoembryonic Antigen

Embodiments herein are directed to methods of accurately measuring carcinoembryonic antigen in a biological sample, the method comprising: diluting the biological sample with a diluent to form a diluted sample when an amylase level in the biological sample is less than a pre-determined amylase threshold between about 10,000 and about 20,000 units; wherein diluting the biological sample with a diluent comprises diluting the biological sample in a ratio of biological sample to diluent between about 1:10 and about 1:50; and measuring carcinoembryonic antigen in the diluted sample. Some embodiments further comprise measuring amylase level in a biological sample. In some embodiments, the biological sample is undiluted. In some embodiments, the biological sample is selected from pancreatic fluid, pancreatic cyst fluid and combinations thereof. In some embodiments, the pre-determined amylase threshold is about 10,000 units, about 15,000 units, or about 20,000 units. In some embodiments, diluting the biological sample with a diluent comprises diluting the biological sample with diluent in a ratio of biological sample to diluent of about 1:40. In some embodiments, diluting the biological sample with a diluent comprises diluting the biological sample with a diluent in a ratio of biological sample to diluent of about 1:10. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 μL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, the biological sample is selected from pancreatic fluid, pancreatic cyst fluid and combinations thereof. In some embodiments, the presence of carcinoembryonic antigen above a predetermined carcinoembryonic antigen threshold in the diluted sample is indicative of a pathological condition. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml. In yet other embodiments, the carcinoembryonic antigen level threshold is determined based on clinical relevance, by the treating physician or a combination thereof.

In some embodiments, the pathological condition is selected from a neoplastic condition, a non-neoplastic condition and a combination thereof. In some embodiments, the neoplastic condition is selected from colorectal carcinoma, gastric carcinoma, pancreatic carcinoma, cholangiocarcinoma, intraductal papillary mucinous neoplasm (IPMN), lung carcinoma, breast carcinoma, medullary thyroid carcinoma, mucinous cystic neoplasm, and combinations thereof.

In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

Figure 2:
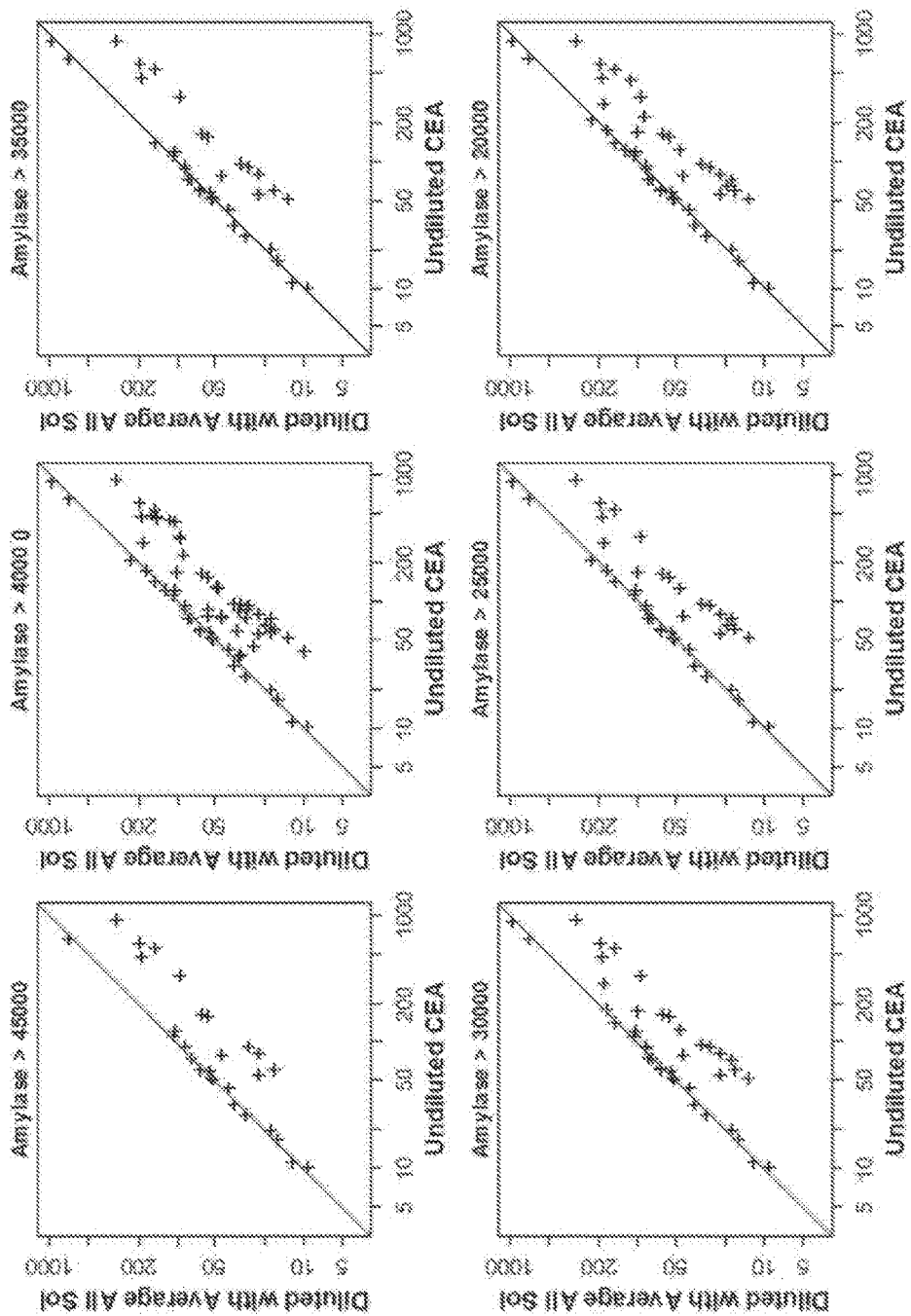
FIG. 2 shows neat carcinoembryonic antigen (CEA) levels in pancreatic cyst fluid samples plotted against CEA levels in pancreatic cyst fluid samples diluted with saline at a ratio of sample to saline of 1:10 or with Diluent Universal at a ratio of sample to diluent of 1:10. Samples are plotted based on amylase levels (e.g. greater than 15,000, 20,000, 25,000, 30,000 or 40,000).
Figure 3:
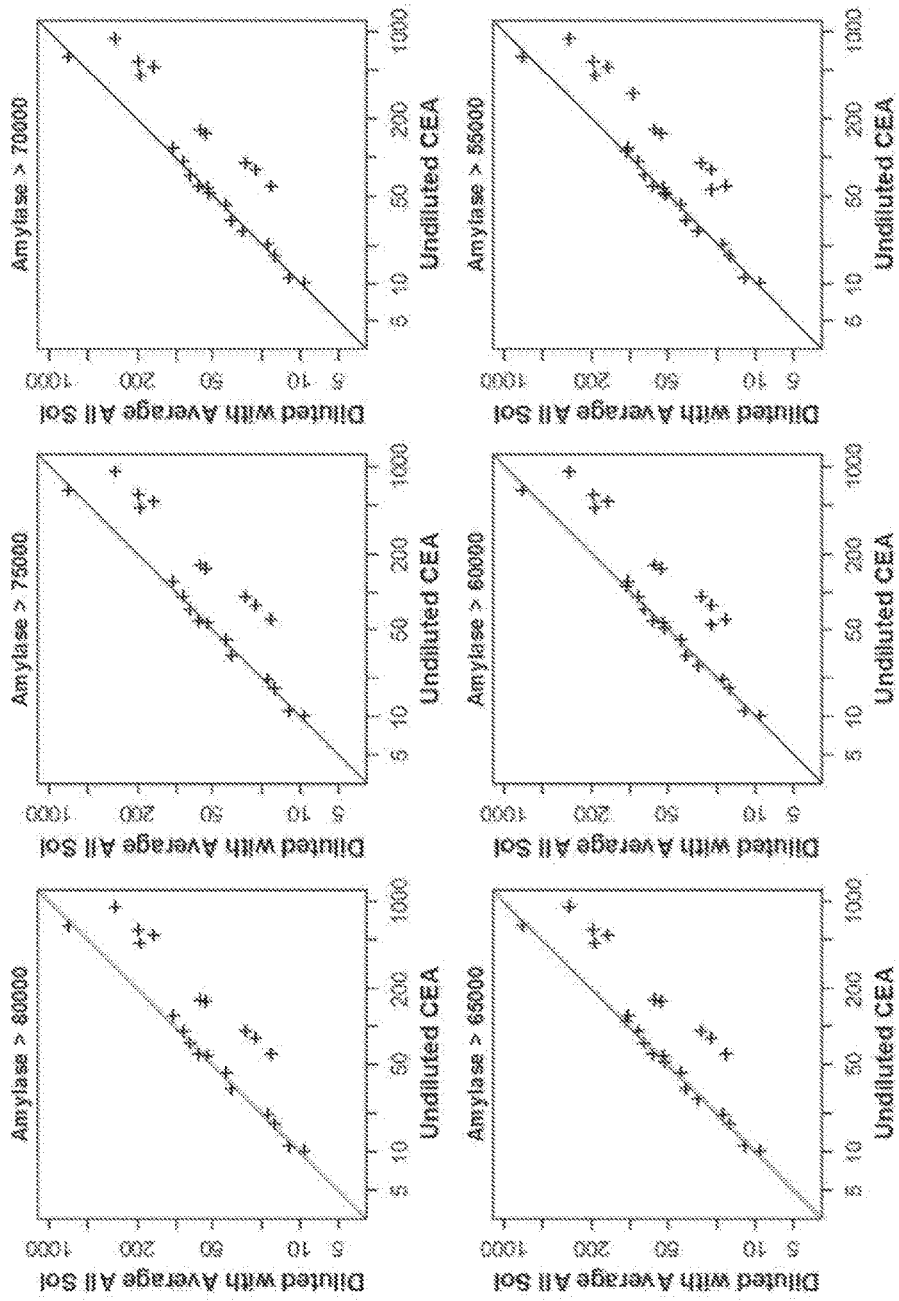
FIG. 3 shows neat carcinoembryonic antigen (CEA) levels in pancreatic cyst fluid samples plotted against CEA levels in pancreatic cyst fluid samples diluted with saline at a ratio of sample to saline of 1:10 or with Diluent Universal at a ratio of sample to diluent of 1:10 for samples with amylase levels greater than 55,000, 60,000, 65,000, 70,000, 75,000 or 80,000. Samples are plotted based on amylase levels.
Figure 4:
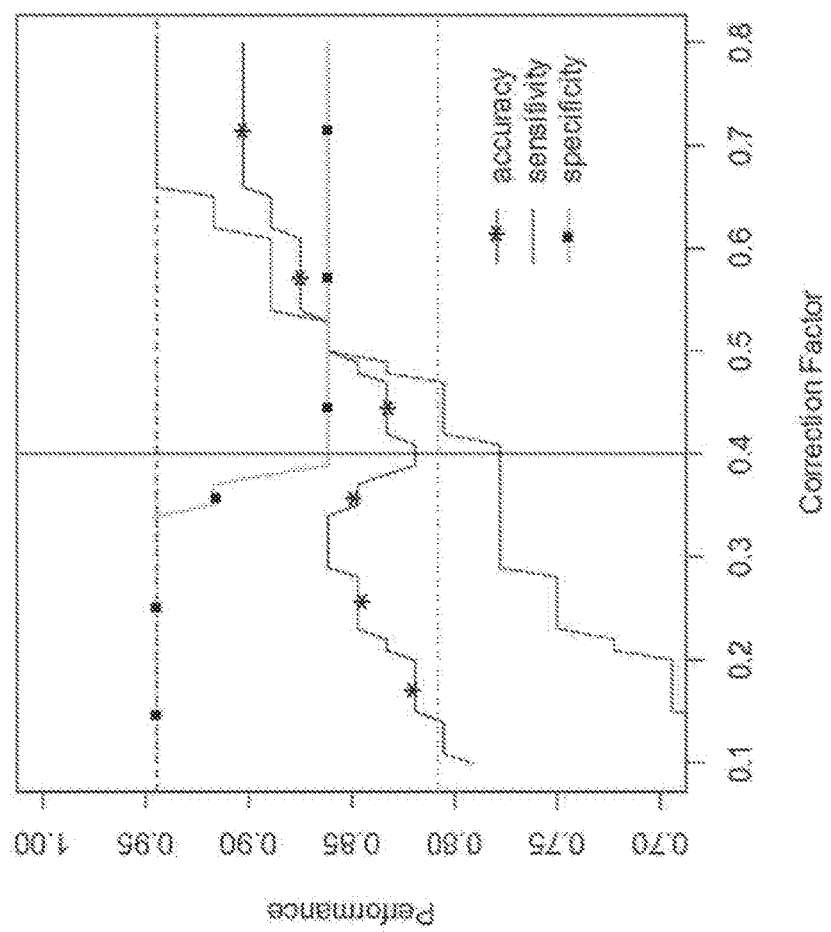
FIG. 4 shows the effect of different correction factors after 1:10 dilution with saline of pancreatic cyst fluid with amylase values greater than 15,000 on the ability (accuracy, sensitivity, and specificity) to detect mucinous pancreatic cysts with CEA values of greater than or equal to 192, which can be indicative of the presence of a mucinous cyst.

FIG. 1 depicts neat carcinoembryonic antigen (CEA) levels in pancreatic cyst fluid samples plotted against CEA levels in pancreatic cyst fluid samples diluted with saline at a ratio of sample to saline of 1:10 at a variety of amylase levels (less than 40,000, 30,000, 25,000, 25,000, 20,000, 15,000 or 10,000). FIG. 2 depicts neat carcinoembryonic antigen (CEA) levels in pancreatic cyst fluid samples plotted against CEA levels in pancreatic cyst fluid samples diluted with saline at a ratio of sample to saline of 1:10 or with Diluent Universal at a ratio of sample to diluent of 1:10 for samples with amylase levels above 15,000, 20,000, 25,000, 30,000, or 40,000. FIG. 3 depicts neat carcinoembryonic antigen (CEA) levels in pancreatic cyst fluid samples plotted against CEA levels in pancreatic cyst fluid samples diluted with saline at a ratio of sample to saline of 1:10 or with Diluent Universal at a ratio of sample to diluent of 1:10 for samples with amylase levels above 55,000, 60,000, 65,000, 70,000, 75,000, or 80,000. Applying a correction factor of around 0.7 to CEA measurements of cyst fluid specimens with amylase values greater than 15000 proved most accurate and sensitive for detection of mucinous cysts when a mucinous cyst is deemed present based on CEA levels greater than or equal to 192 ng/mL. In some embodiments, when amylase levels are low (less than 15,000 units), samples diluted with a diluent such as but not limited to saline or Diluent Universal at a ratio of sample to diluent of 1:10 results in CEA level measurements that are comparable to those in neat pancreatic cyst fluid samples. As can be seen in FIGS. 1, 2, and 3, CEA levels in pancreatic cyst fluid samples diluted with saline at a ratio of sample to saline of 1:10 with amylase levels below 20,000 display a high degree of accuracy to neat carcinoembryonic antigen (CEA) levels in pancreatic cyst fluid samples. In contrast, CEA levels in pancreatic cyst fluid samples diluted with saline at a ratio of sample to saline of 1:10 with amylase levels above 20,000 display a lesser degree of accuracy to neat carcinoembryonic antigen (CEA) levels in pancreatic cyst fluid samples. The higher the amylase level in a sample, the less accurate the CEA level reading when the sample is diluted with saline at a ratio of sample to saline of 1:10 compared with neat carcinoembryonic antigen (CEA) levels in pancreatic cyst fluid samples. When amylase levels are high (greater than 15,000 units), CEA levels in samples diluted with a diluent such as but not limited to saline or Diluent Universal at a ratio of sample to saline of 1:10 appear to overestimate CEA values compared with undiluted samples. A linear regression analysis of CEA levels from undiluted, neat samples versus CEA levels in samples diluted in saline at a sample to saline ratio of 1:10 reveals that a correction factor of about 0.7 increases accuracy of CEA level measurements in samples with amylase levels greater than 15,000 units. In addition, FIG. 4 shows that a correction factor of 0.7 results in the best accuracy and specificity. In some embodiments, the CEA level obtained in the sample diluted with saline in a sample to saline ratio of 1:10 is multiplied by the correction factor. In some embodiments the correction factor is about 0.7.

Figure 5:
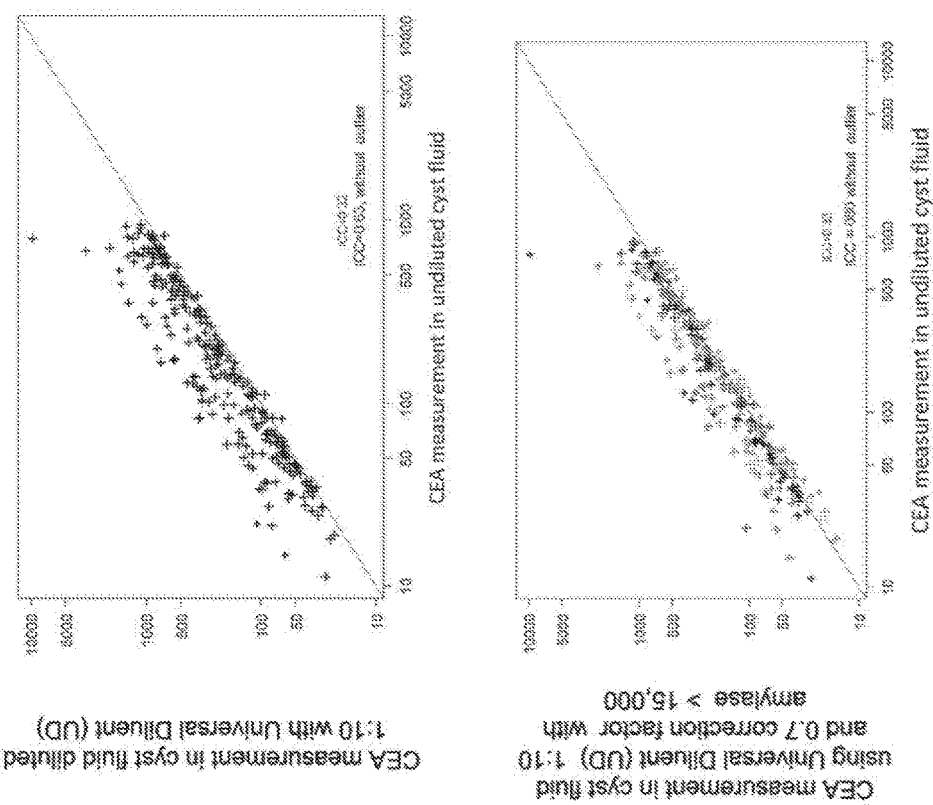
FIG. 5 shows the correlation of carcinoembryonic antigen (CEA) levels in 266 undiluted cyst fluid samples versus CEA levels in cyst fluid samples diluted 1:10 with Diluent Universal (top graph) and 1:10 with Diluent Universal followed by application of a correction factor of 0.7 for samples with amylase levels of greater than 15,000 (bottom graph). The intraclass correlation coefficient (ICC) using Diluent Universal=0.32 (0.63 without outlier data point) and intraclass correlation coefficient (ICC) using Diluent Universal followed by application of a correction factor of 0.7=0.33 (0.80 without outlier data point). Black crosses represent samples with amylase levels equal to, or below 15,000 and gray crosses represent samples with amylase levels greater than 15,000.

In some embodiments, the methods disclosed herein result in an improved intraclass correlation coefficient. FIG. 5 shows the correlation of carcinoembryonic antigen (CEA) levels in 266 undiluted samples versus CEA levels in samples diluted 1:10 with Diluent Universal (top graph) and 1:10 with Diluent Universal followed by application of a correction factor of 0.7 for samples with amylase levels of greater than 15,000 (bottom graph). The intraclass correlation coefficient (ICC) using Diluent Universal was 0.32 (0.63 without outlier data point) and intraclass correlation coefficient (ICC) using saline followed application of a correction factor of 0.7 was 0.33 (0.80 without outlier data point).

Figure 7:
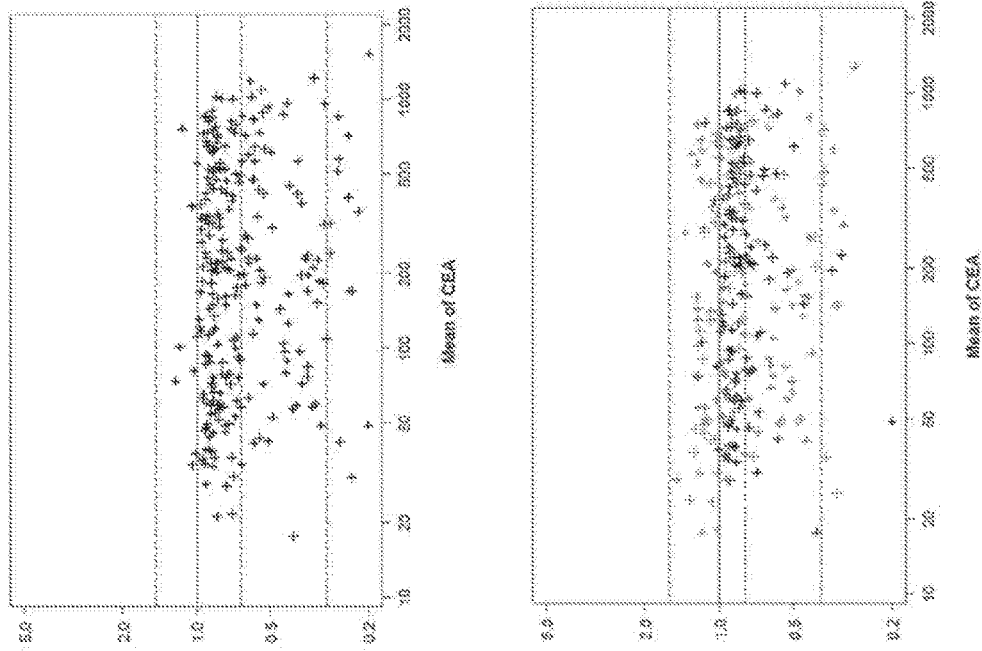
FIG. 7 shows Bland-Altman bias plots examining a ratio of undiluted sample CEA levels to diluted sample CEA levels (diluted 1:10 with Diluent Universal) showing statistically significant bias (top graph; bias with outlier data point=0.6553449, p-value<2.2e-16; bias without outlier data point=0.6605572, p-value<2.2e-16), and examined using a ratio of undiluted sample CEA levels to diluted sample CEA levels (diluted 1:10 with Diluent Universal followed by application of a correction factor of 0.7 for samples with amylase levels of greater than 15,000) showing a statistically significant but reduced bias (bottom graph; bias with outlier data point=0.7864442, p-value<2.2e-16; bias without outlier data point=0.7932449, p-value<2.2e-16). Black crosses represent samples with amylase levels equal to or below 15,000 and gray crosses represent samples with amylase levels greater than 15,000.

Bland-Altman bias plots were created examining a ratio of undiluted sample CEA levels to diluted sample CEA levels. A bias score of 1 indicated no bias. As can be seen in FIG. 7, the mean bias for cyst fluid samples diluted 1:10 with Diluent Universal was 0.6553449 (p-value<2.2e-16) (Without outlier data point, bias was 0.6605572, p-value<2.2e-16) indicative of a statistically significant bias (top graph). In comparison, the mean bias for cyst fluid samples diluted 1:10 with Diluent Universal followed by application of a correction factor of 0.7 when amylase levels are greater than 15,000 was 0.7864442 (p-value<2.2e-16) (without outlier, bias was 0.7932449 (p-value<2.2e-16)) indicative of a statistically significant but reduced bias (bottom graph).

Figure 6:
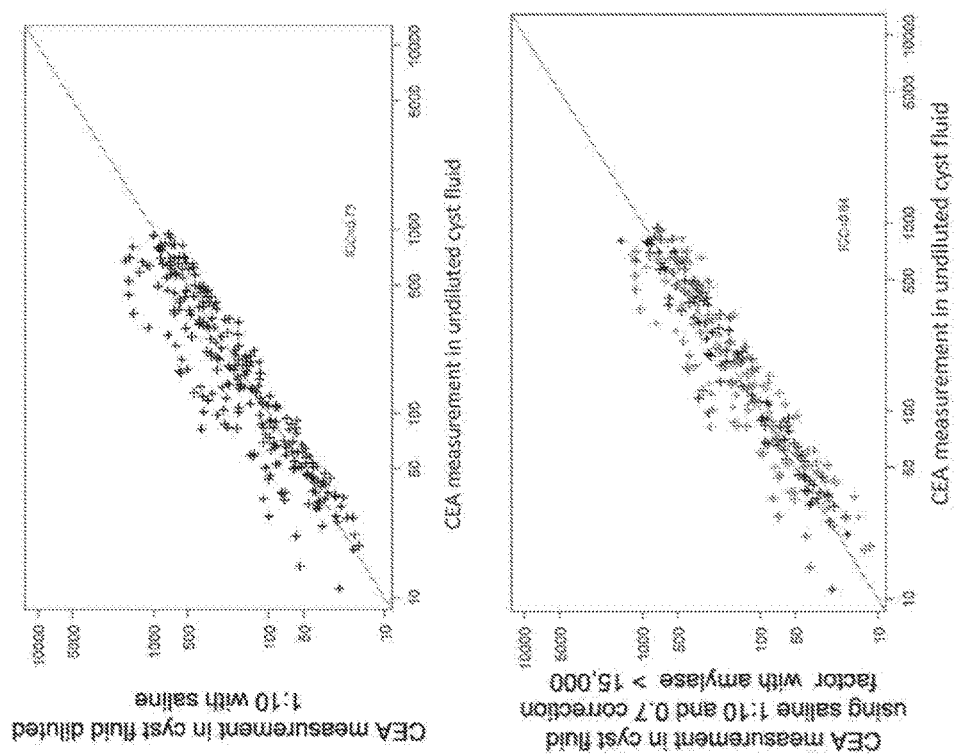
FIG. 6 shows the correlation of carcinoembryonic antigen (CEA) levels in 266 undiluted cyst fluid samples versus CEA levels in cyst fluid samples diluted 1:10 with saline (top graph) and 1:10 with saline followed by application of a correction factor of 0.7 for samples with amylase levels of greater than 15,000 (bottom graph). The intraclass correlation coefficient (ICC) using saline=0.73 and intraclass correlation coefficient (ICC) using saline followed by application of a correction factor of 0.7=0.84. Black crosses represent samples with amylase levels equal to or below 15,000 and gray crosses represent samples with amylase levels greater than 15,000.

FIG. 6 shows the correlation of carcinoembryonic antigen (CEA) levels in 266 undiluted samples versus CEA levels in samples diluted 1:10 with saline (top graph) and 1:10 with saline followed application of a correction factor of 0.7 for samples with amylase levels of greater than 15,000 (bottom graph). The intraclass correlation coefficient (ICC) using saline was 0.73 and the intraclass correlation coefficient (ICC) using saline followed application of a correction factor of 0.7 was 0.84.

Figure 8:
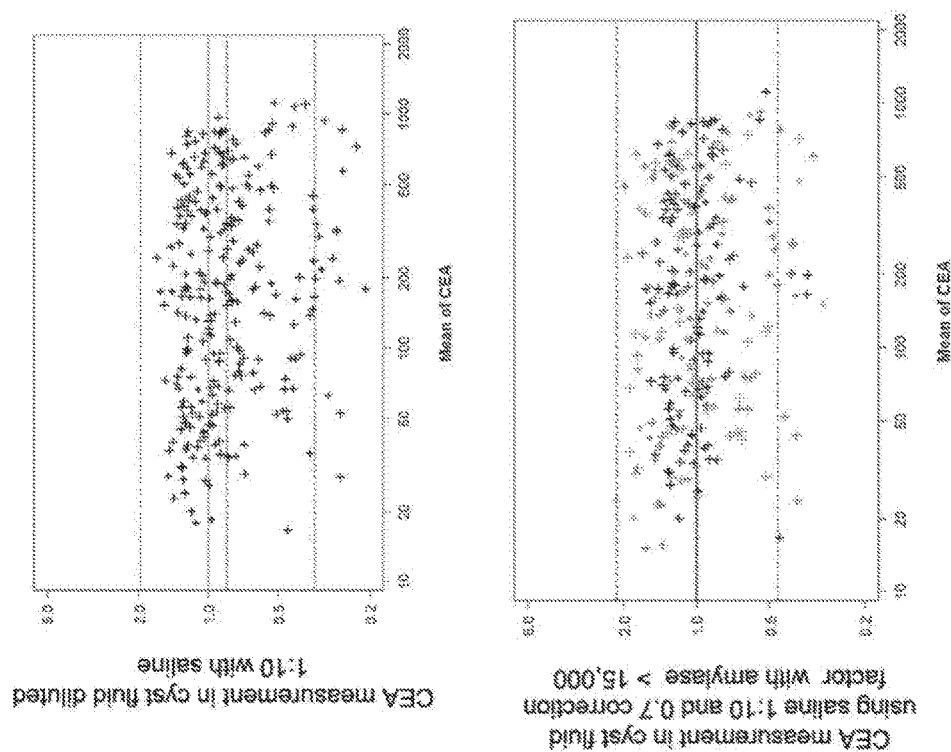
FIG. 8 shows Bland Altman bias plots examining a ratio of undiluted sample CEA levels to diluted sample CEA levels (diluted 1:10 with saline) showing statistically significant bias (top graph; bias=0.8304916, p-value=6.115e-11), and examined using a ratio of undiluted sample CEA levels to diluted sample CEA levels (diluted 1:10 with saline followed by application of a correction factor of 0.7 for samples with amylase levels of greater than 15,000) showing no statistically significant bias (bottom graph; bias=0.9966283, p-value=0.8881). Black crosses represent samples with amylase levels equal to or below 15,000 and gray crosses represent samples with amylase levels greater than 15,000.

Bland-Altman bias plots were created examining a ratio of undiluted sample CEA levels to diluted sample CEA levels. A bias score of 1 indicated no bias. As can be seen in FIG. 8, the mean bias for cyst fluid samples diluted 1:10 with saline was 0.8304916 (p-value=6.15 e-11). In comparison, there was no statistically significant bias for cyst fluid samples diluted 1:10 with saline followed by application of a correction factor of 0.7 when amylase levels are greater than 15,000 (0.9966283, p-value=0.8881). These data are indicative that dilution of samples with diluents such as, but not limited to saline and Diluent Universal, followed by application of a correction factor when amylase levels in the sample are greater than 15,000 results in better reproduction of CEA measurements in undiluted samples. These data also indicate that there is decreased variability (increased ICC measurements) and less bias with dilution of samples with diluents such as, but not limited to saline and Diluent Universal followed by application of a correction factor when amylase levels in the sample are greater than 15,000.

In some embodiments, a correction factor is applied when amylase levels in a sample diluted 1:40 with diluent are greater than 15,000. In some embodiments, the correction factor is about 0.7. In some embodiments, the diluent is saline, Diluent Universal or a combination thereof. In some embodiments, a correction factor is applied when amylase levels in a sample diluted 1:10 with diluent are greater than 15,000. In some embodiments, the correction factor is about 0.7. In some embodiments, the diluent is saline, Diluent Universal or a combination thereof. In some embodiments, a correction factor is applied when amylase levels in a sample diluted 1:40 with saline are greater than 15,000. In some embodiments, the correction factor is about 0.7. In some embodiments, a correction factor is applied when amylase levels in a sample diluted 1:10 with saline are greater than 15,000. In some embodiments, the correction factor is about 0.7. Additional studies performed show the correlation of carcinoembryonic antigen (CEA) levels in 72 undiluted samples versus CEA levels in samples diluted 1:10 with saline followed application of a correction factor of 0.7 where amylase levels in diluted samples are greater than 15,000. In this study, results were as follows: ICC=0.91; mean bias=0.94 (p-value=0.139). Yet another study shows the correlation of carcinoembryonic antigen (CEA) levels in 204 undiluted samples versus CEA levels in samples diluted 1:10 with saline followed application of a correction factor of 0.7 where amylase levels in diluted samples are greater than 15,000. In this study, results were as follows: ICC=0.88; mean bias=1.04 (p-value=0.0996) indicating improved variability and no bias when 1:10 dilution is used followed by application of a correction factor of 0.7 in samples with amylase levels above 15,000. Table 1 illustrates the results from the studies described herein for various methods of analyzing CEA levels and results indicate that using an amylase cut off of 15,000 and a sample to saline dilution of 1:10 to 1:40 wherein a correction factor of 0.7 is applied to samples with amylase levels above 15,000 resulted in the superior results and more accurate CEA measurements compared to not implementing the correction factor based on the 15,000 amylase cut off.

antigen level in the diluted biological sample; multiplying the carcinoembryonic antigen level by a correction factor to obtain a corrected carcinoembryonic antigen level. In some embodiments, the correction factor is about 0.7.

In some embodiments, the correction factor applied may vary. In some embodiments, the correction factor to be applied may range from about 0.1 to about 0.8. In some embodiments, the correction factor to be applied when CEA levels greater than 15,000 is about 0.7. In some embodiments the correction factor to be applied is determined as follows: a separate linear regression without intercept may be performed by regressing undiluted CEA (neat) values versus CEA values for samples diluted in diluent at a sample to diluent ratio of about 1:10 for subsets of samples where amylase levels is greater than about 15,000. The resulting estimated coefficient from the above-described linear regressions can be used as the correction factor measurement of CEA levels in a sample diluted with diluent at a sample to diluent ratio of 1:10. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification ($\alpha$-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

TABLE 1

Summary of ICC and Bias for each method of dilution compared to neat CEA values based on not applying (rows 1 and 2) or applying (rows 3 and 4) the correction factor of 0.7 based on Amylase cut off of 15,000 for specimens diluted 1:10 or 1:40 with saline or diluent universal (UD).

| Row # | | Training Set | | | Verification Set w/ out outlier | | |
|---|---|---|---|---|---|---|---|
| | | ICC | Bias | p-value | ICC | Bias | p-value |
| 1 | Neat vs. 1:10 Saline | 0.87 | 0.78 | 9.24E−06 | 0.79 | 0.87 | 1.54E−05 |
| 2 | Neat vs. 1:10 UD | Not Done | Not Done | Not Done | Not Done | Not Done | Not Done |
| 3 | Amylase cut-off (1:40) & CF 0.7 | 0.89 | 0.98 | 7.37E−01 | 0.84 | 1.13 | 1.52E−04 |
| 4 | Amylase cut-off (1:10) & CF 0.7 | 0.91 | 0.94 | 1.39E−01 | 0.88 | 1.04 | 9.96E−02 |

In some embodiments, where amylase levels in a particular sample are below 15,000, the sample is diluted with a diluent at a sample to diluent ratio of 1:40 but no correction factor is used. In some embodiments, where amylase levels in a particular sample are below 15,000, the sample is diluted with a diluent at a sample to diluent ratio of 1:10 but no correction factor is used.

Some embodiments are directed to methods of accurately measuring carcinoembryonic antigen in a biological sample, the method comprising: diluting the biological sample with a diluent at a ratio of biological sample to diluent of about 1:10 to about 1:50 to form a diluted biological sample, wherein the amylase level in the biological sample is greater than a pre-determined amylase threshold between about 10,000 and about 20,000 units; measuring carcinoembryonic In some embodiments the correction factor to be applied is determined as follows: a separate linear regression without intercept may be performed by regressing undiluted CEA (neat) values versus CEA values for samples diluted in a diluent at a sample to diluent ratio of about 1:40 for subsets of samples where amylase levels is greater than about 15,000. The resulting estimated coefficient from the above-described linear regressions can be used as the correction factor measurement of CEA levels in a sample diluted with diluent at a sample to diluent ratio of 1:40. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

Some embodiments further comprise measuring amylase levels in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with a diluent comprises diluting the biological sample in a ratio of sample to diluent of about 1:10. In some embodiments, diluting the biological sample with a diluent comprises diluting the biological sample in a ratio of sample to diluent of about 1:40. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 μL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, a corrected carcinoembryonic antigen level above a predetermined carcinoembryonic antigen threshold is indicative of a pathological condition. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml. In some embodiments, the pathological condition is selected from a neoplastic condition, a non-neoplastic condition and a combination thereof. In some embodiments, the neoplastic condition is selected from colorectal carcinoma, gastric carcinoma, cholangiocarcinoma, pancreatic carcinoma, intraductal papillary mucinous neoplasm (IPMN), lung carcinoma, breast carcinoma, medullary thyroid carcinoma, mucinous cystic neoplasm, and combinations thereof. In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

Methods of Identifying a Mucinous Cyst

Some embodiments are directed to methods of identifying a mucinous cyst in a subject, the method comprising: diluting the biological sample with a diluent when an amylase level in the biological sample is less than a pre-determined amylase threshold between about 10,000 and about 20,000 units, to form a diluted sample, wherein diluting the biological sample with a diluent comprises diluting the biological sample in a ratio of biological sample to diluent between about 1:10 and about 1:50; and measuring carcinoembryonic antigen level in the diluted sample; wherein a carcinoembryonic antigen level above a predetermined carcinoembryonic antigen level threshold in the saline diluted sample is indicative of a mucinous cyst.

Some embodiments further comprise obtaining a biological sample from the subject. In some embodiments, the biological sample is selected from pancreatic fluid, pancreatic cyst fluid and combinations thereof. Some embodiments further comprise measuring amylase levels in a biological sample. In some embodiments, the biological sample is undiluted.

In some embodiments, the pre-determined amylase threshold is about 10,000 units, about 15,000 units, or about 20,000 units. In some embodiments, diluting the biological sample with diluent comprises diluting the biological sample in a ratio of sample to diluent of about 1:40. In some embodiments, diluting the biological sample with a diluent comprises diluting the biological sample in a ratio of sample to diluent of about 1:10. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml.

In some embodiments, the biological sample is not present in sufficient volume to accurately measure carcinoembryonic antigen levels. In some embodiments, the biological sample has a high viscosity. In some embodiments, the high viscosity is due to the presence of mucin in the neat biological sample. In some embodiments, the carcinoembryonic antigen levels in the biological sample exceed the measurement capabilities of an instrument being used to measure carcinoembryonic antigen.

Some embodiments are directed to methods of identifying a mucinous cyst in a subject, the method comprising: diluting the biological sample with a diluent at a ratio of biological sample to diluent of about 1:10 to about 1:50 to form a diluted biological sample, wherein the amylase levels in the biological sample are greater than a pre-determined amylase threshold between about 10,000 and about 20,000 units; measuring carcinoembryonic antigen level in the diluted biological sample; multiplying the carcinoembryonic antigen level of the diluted biological sample by a correction factor to obtain a corrected carcinoembryonic antigen level; and wherein a corrected carcinoembryonic antigen level of above a predetermined carcinoembryonic antigen threshold is indicative of a mucinous cyst. In some embodiments, the correction factor is about 0.7.

Some embodiments further comprise obtaining a biological sample from the subject. Some embodiments further comprise measuring amylase levels in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with a diluent comprises diluting the biological sample in a ratio of biological sample to diluent of about 1:10. In some embodiments, diluting the biological sample with diluent comprises diluting the biological sample in a ratio of sample to diluent of about 1:40. In some embodiments, the biological sample can be diluted in an aqueous salt solution. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the carcinoembryonic antigen level threshold is between about 5 ng/ml and about 1,000 ng/ml. In some embodiments, the carcinoembryonic antigen level threshold is about 192 ng/ml or about 400 ng/ml.

In some embodiments, the biological sample is not present in sufficient volume to accurately measure carcinoembryonic antigen levels. In some embodiments, the minimum volume to accurately measure CEA is about 200 µL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

Methods of Treating a Pathological Condition

Some embodiments are directed to a method of treating a pathological condition in a subject in need thereof, the method comprising measuring CEA in a biological sample from the subject, and administering to the subject an effective amount of a treatment modality for the pathology wherein the presence of CEA in the biological sample is above a pre-determined threshold.

In some embodiments, measuring CEA in a biological sample from the subject comprises diluting the biological sample with a diluent to form a diluted sample when an amylase level in the biological sample is less than a pre-determined amylase threshold between about 10,000 and about 20,000 units; wherein diluting the biological sample with diluent comprises diluting the biological sample in a ratio of biological sample to diluent between about 1:10 and about 1:50; and measuring carcinoembryonic antigen in the diluted sample. Some embodiments further comprise measuring amylase level in a biological sample. In some embodiments, the pre-determined amylase threshold is about 10,000 units, about 15,000 units, or about 20,000 units.

In some embodiments, the biological sample is undiluted. In some embodiments, the biological sample is selected from pancreatic fluid, pancreatic cyst fluid and combinations thereof. In some embodiments, the biological sample is selected from pancreatic fluid, pancreatic cyst fluid and combinations thereof.

In some embodiments, diluting the biological sample with saline comprises diluting the biological sample with a diluent in a ratio of biological sample to diluent of about 1:40. In some embodiments, diluting the biological sample with a diluent comprises diluting the biological sample with diluent in a ratio of biological sample to diluent of about 1:10. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification (α-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 µL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, the presence of carcinoembryonic antigen above a predetermined carcinoembryonic antigen threshold in the saline diluted sample is indicative of a pathological condition. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml. In some embodiments, the pathological condition is selected from a neoplastic condition, a non-neoplastic condition and a combination thereof. In some embodiments, the neoplastic condition is selected from colorectal carcinoma, gastric carcinoma, pancreatic carcinoma, cholangiocarcinoma, intraductal papillary mucinous neoplasm (IPMN), lung carcinoma, breast carcinoma, medullary thyroid carcinoma, and combinations thereof. In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

In some embodiments, measuring CEA in a biological sample from the subject comprises diluting the biological sample with a diluent at a ratio of biological sample to diluent of about 1:10 to about 1:50 to form a diluted biological sample, wherein the amylase level in the biological sample is greater than a pre-determined amylase threshold between about 10,000 and about 20,000 units; measuring carcinoembryonic antigen level in the diluted biological sample; multiplying the carcinoembryonic antigen level by a correction factor to obtain a corrected carcinoembryonic antigen level. In some embodiments, the correction factor is about 0.7.

Some embodiments further comprise measuring amylase levels in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with diluent comprises diluting the biological sample in a ratio of sample to diluent of about 1:10. In some embodiments, diluting the biological sample with diluent comprises diluting the biological sample in a ratio of sample to diluent of about 1:40. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification ($\alpha$-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 µL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, a corrected carcinoembryonic antigen level above a predetermined carcinoembryonic antigen threshold is indicative of a pathological condition. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml. In some embodiments, the pathological condition is selected from a neoplastic condition, a non-neoplastic condition and a combination thereof. In some embodiments, the neoplastic condition is selected from colorectal carcinoma, gastric carcinoma, cholangiocarcinoma, pancreatic carcinoma, intraductal papillary mucinous neoplasm (IPMN), lung carcinoma, breast carcinoma, medullary thyroid carcinoma, mucinous cystic neoplasm, and combinations thereof. In some embodiments, the non-neoplastic condition is selected from ulcerative colitis, pancreatitis, pancreatic cysts, pancreatic masses, biliary strictures, cirrhosis, chronic obstructive pulmonary disease, Crohn's disease, intraductal papillary mucinous neoplasm (IPMN), and combinations thereof.

In some embodiments, the treatment modality comprises surgical resection, chemotherapy, drug therapy, biological therapy, gene therapy, vaccine therapy, radiation therapy, photodynamic therapy, hypothermic therapy, laser therapy and combinations thereof.

Some embodiments are directed to a method of treating pancreatic carcinoma in a subject in need thereof, the method comprising measuring CEA in a biological sample from the subject, and administering to the subject an effective amount of a treatment modality for the pathology wherein the presence of CEA in the biological sample is above a pre-determined threshold.

In some embodiments, measuring CEA in a biological sample from the subject comprises diluting the biological sample with a diluent to form a diluted sample when an amylase level in the biological sample is less than a pre-determined amylase threshold between about 10,000 and about 20,000 units; wherein diluting the biological sample with a diluent comprises diluting the biological sample in a ratio of biological sample to diluent between about 1:10 and about 1:50; and measuring carcinoembryonic antigen in the diluted sample.

Some embodiments further comprise measuring amylase level in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with diluent comprises diluting the biological sample with saline in a ratio of biological sample with diluent comprises diluting the biological sample with diluent in a ratio of biological sample to diluent of about 1:40. In some embodiments, diluting the biological sample with diluent comprises diluting the biological sample with diluent in a ratio of biological sample to diluent of about 1:10. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification ($\alpha$-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 µL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, the biological sample is selected from pancreatic fluid, pancreatic cyst fluid and combinations thereof. In some embodiments, the presence of carcinoembryonic antigen above a predetermined carcinoembryonic antigen threshold in the saline diluted sample is indicative of pancreatic carcinoma. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml.

In some embodiments, measuring CEA in a biological sample from the subject comprises diluting the biological sample with a diluent at a ratio of biological sample to diluent of about 1:10 to about 1:50 to form a diluted biological sample, wherein the amylase level in the biological sample is greater than a pre-determined amylase threshold between about 10,000 and about 20,000 units; measuring carcinoembryonic antigen level in the diluted biological sample; multiplying the carcinoembryonic antigen level by a correction factor to obtain a corrected carcinoembryonic antigen level. In some embodiments, the correction factor is about 0.7.

Some embodiments further comprise measuring amylase levels in a biological sample. In some embodiments, the biological sample is undiluted. In some embodiments, the biological sample is selected from pancreatic fluid, pancreatic cyst fluid and combinations thereof.

In some embodiments, the pre-determined amylase threshold is about 10,000 units, about 15,000 units, or about 20,000 units. In some embodiments, diluting the biological sample with a diluent comprises diluting the biological sample in a ratio of sample to diluent of about 1:10. In some embodiments, diluting the biological sample with saline comprises diluting the biological sample in a ratio of sample to diluent of about 1:40. In some embodiments, the diluent is an aqueous salt solution. Examples of suitable aqueous salt solutions include but are not limited to saline, Diluent Universal (Elecsys Diluent Universal, Roche Diagnostics), Tyrode's solution, lactated Ringer's Solution, acetated Ringer's solution, TRIS-buffered saline (TBS), Hank's balanced salt solution (HBSS), Earle's balanced salt solution (EBSS), Standard saline citrate (SSC), HEPES-buffered saline (HBS), Gey's balanced salt solution (GBSS), minimum essential medium Eagle alpha modification ($\alpha$-MEM), phosphate buffered saline (PBS), and combinations thereof. In some embodiments, the biological sample is diluted in water. In some embodiments, the diluent is saline. In some embodiments, the diluent is Diluent Universal (Elecsys Diluent Universal, Roche Diagnostics).

In some embodiments, the biological sample is not present in sufficient volume to accurately measure carcinoembryonic antigen levels. In some embodiments, the minimum volume to accurately measure CEA is about 200 µL. In some embodiments, the biological sample has a high viscosity. In some embodiments, the high viscosity is due to the presence of mucin in the biological sample. In some embodiments, the carcinoembryonic antigen levels in the biological sample exceed the measurement capabilities of an instrument being used to measure carcinoembryonic antigen levels. In some embodiments, measuring CEA comprises measuring CEA with a Roche Modular Analytics E170 instrument.

In some embodiments, a corrected carcinoembryonic antigen level above a predetermined carcinoembryonic antigen threshold is indicative of pancreatic carcinoma. In some embodiments, the carcinoembryonic antigen level threshold is between about 5 ng/ml and about 1,000 ng/ml. In some embodiments, the carcinoembryonic antigen level threshold is about 192 ng/ml, or about 400 ng/ml.

In some embodiments, the treatment modality comprises surgical resection, chemotherapy, drug therapy, biological therapy, gene therapy, vaccine therapy, radiation therapy, photodynamic therapy, hypothermic therapy, laser therapy and combinations thereof.

This invention and embodiments illustrating the method and materials used may be further understood by reference to the following non-limiting examples.

EXAMPLES

Example 1—Analytical Validation of Dilution of Pancreatic Fluid Specimens for CEA Testing Purpose To determine if the New Method for dilution of pancreatic cyst fluid specimens for CEA testing is improved compared to the clinical method through establishing analytical linearity, accuracy, precision, sensitivity and specificity.

Introduction

CEA measurements in diluted pancreatic cyst fluids have been found to not accurately reflect the original neat pancreatic cyst fluid CEA value. RedPath Integrated Pathology has developed a unique testing method to address this issue. A pancreatic cyst fluid is inherently a lower volume specimen type, and often times the volume of the specimen collected does not meet the volume requirement for CEA testing. The ability to perform upfront dilutions on pancreatic cysts specimens and provide an accurate CEA value, as compared to undiluted CEA measurements, was the goal in the development of this methodology improvement.

CEA Method Development

The development process for this methodology evolved through trial and error of different applications and the correlating analyses of each result set. Pancreatic cyst fluids with excess volume were used for all developmental testing of this method, and dilutions performed on specimens were compared to the CEA values obtained from testing the specimens neat (undiluted).

A number of different off-shelf diluents were tested comparatively. During this testing, it was found that Saline showed improvement as a diluent versus Diluent Universal (UD, Roche), which is currently the diluent used to perform dilutions for clinical CEA testing. However, the use of saline alone was not enough to improve the accuracy of the CEA value for all pancreatic cyst fluid specimens when diluted.

An in-house diluent, "Solution CEA", was developed and tested in effort to improve the accuracy of all diluted pancreatic cyst fluid specimens. This diluent was found to be effective on some specimens but to over perform for certain pancreatic cyst fluid specimens. When specimens were tested in parallel with saline and Solution CEA dilutions the comparative data was reviewed and a pattern evolved with the incorporation of the Amylase results into the analysis. It was determined that specimens with an Amylase value of less than 15,000 were more accurate with the use of saline as a diluent when compared to the neat CEA values. However, specimens with an Amylase value of greater than 15,000 were more accurate with the use of Solution CEA as the diluent when compared to the neat CEA values.

As more testing was conducted to verify the method and increase the "n" of specimens tested, it was identified through statistical analysis that the effect of the Solution CEA as a diluents could be mathematically replicated through the use of a correction factor (CF). Different CFs were trained and tested on varying dilution points. It was found through this testing that it was essential to both train and validate the method on data sets with pancreatic cyst fluids divided proportionately, since differ methods of testing were required for specimens based on the Amylase result (please refer to Validation Methods, below).

New CEA Method for Validation

All pancreatic fluid specimens requiring an upfront dilution will be diluted using saline as the diluent, and will be diluted using a 1:10 dilution point. Any specimen that requires a dilution and has an Amylase value of greater than 15,000 will have a correction factor (CF) of 0.7 applied to the CEA value to determine the final CEA result reported.

Example: Amylase=16,000

CEA value after 1:10 dilution=400 (value after adjusted for dilution factor)

Final CEA Result for 1:10 dilution=400 multiplied by 0.7=280

Validation Methods

Linearity, Accuracy, Sensitivity & Specificity

To validate the method for dilution of pancreatic cyst fluid specimens, parallel specimen testing for CEA was completed. Each specimen was diluted in UD (old method) and saline (new method) with re-testing of CEA & Amylase on a neat specimen aliquot for result comparison. The validation specimen set was comprised of an equal number of specimens divided into 4 categories. These four specimen categories are:

High CEA (greater than 192) & High Amylase (greater than 15,000)

Low CEA (less than 192) & High Amylase (greater than 15,000)

High CEA (greater than 192) & Low Amylase (less than 15,000)

Low CEA (less than 192) & Low Amylase (less than 15,000)

For this validation, 92 pancreatic cyst fluid specimens were accrued with 23 specimens in each of the four categories described above. Each specimen was accrued and tested as follows:

1. Daily clinical CEA reaction aliquots and Amylase reaction aliquots were saved that meet the following:
   a. A NEAT CEA result of 20-1000
   b. Reportable Amylase result
2. All specimen aliquots were stored at 4 C until parallel testing was completed.
3. For each specimen identified, the following testing was performed:
   a. Amylase & CEA (on neat specimen) were re-tested-→all remaining specimen volume was saved to perform dilutions listed below.
   b. Prepare a 1:10 dilution for CEA using Diluent Universal
      i. 20 µL of specimen to 180 µL of UD
   c. Serial Dilution Series "D" for 1:10 & 1:40 dilutions in Saline were prepared as follows:
      i. 1:10 dilution for CEA using Saline
         (1) 30 µL of specimen to 270 µL of Saline
      ii. 1:40 dilution using Saline & remaining volume from 1:10 dilution in Saline
         (1) 50 µL of 1:10 in Saline to 150 µL of Saline
         NOTE: 1:40 not required for this validation.
4. Testing was completed as defined by standard operating procedures for the neat CEA & Amylase re-tests, as well as the 1:10 dilutions in UD and Saline for CEA testing. All testing was performed on the same day.
5. All specimen aliquots, both NEAT and diluted, were stored at 4° C. after testing was completed.
6. Specimens were accrued and tested as received.

Precision

To determine precision, pancreatic cyst fluid specimens were collected to perform parallel specimen testing for CEA. Prior to the precision study, each specimen was re-tested for CEA & Amylase using a neat specimen aliquot for result comparison. Parallel testing was performed in triplicate on specimen dilutions in UD (old method) and Saline (new method). Each dilution was tested over 3 different run scenarios:

Run 1=DAY 1: Operator 1

Run 2=DAY 1: Operator 2

Run 3=DAY 2: Operator 1

For this validation, 16 specimens were accrued with 4 specimens in each of the four categories described above in the "Linearity, Accuracy, Sensitivity & Specificity" section. Each specimen was accrued and tested as follows:

1. Specimens were collected over a period of time that met the following:
   a. A NEAT CEA result of 20-1000
   b. Reportable Amylase result
   c. At least 650 µL of remaining fluid
2. Specimens collected were aliquoted, labeled, and stored at 4° C.
3. Specimens were re-tested to confirm original results prior to proceeding with Step 4, as follows:
   a. Re-tested specimens Neat for CEA
   b. Re-tested specimens for Amylase
4. Eight specimens with the following (CEA and Amylase clinical reaction aliquots may have been saved and used to re-test CEA and Amylase and/or for dilution preparations from NEAT reaction aliquots):
   a. Clinical Amylase result=LESS THAN 15,000
   b. Clinical CEA result=20-1000
      (1) 4 MED/HIGH specimens (192<CEA<400-1000)
      (2) 4 LOW specimens (CEA<192)
5. Eight specimens with the following (CEA and Amylase clinical reaction aliquots may have been saved and used to re-test CEA and Amylase and/or for dilution preparations from NEAT reaction aliquots):
   a. Clinical Amylase result=GREATER THAN 15,000
   b. Clinical CEA result=0-1000 (instrument range)
      (1) 4 MED/HIGH specimens (192<CEA<400-1000)
      (2) 4 LOW specimens (CEA<192)
6. For each specimen identified, triplicate tests were run for all dilution points (see step 7, below) and tested over a 2-day period, as listed below:
   a. Run 1=DAY 1: Operator 1
   b. Run 2=DAY 1: Operator 2
   c. Run 3=DAY 2: Operator 1
7. Dilutions for the identified specimens tested as described in step 6 are listed below:
   a. 1:10 dilution for CEA using UD
      (1) 60 µL of specimen to 540 µL of UD
         (i) Prepared 3 aliquots (A, B & C) at 200 ul.
         (ii) 1 Dilution/3 aliquots→3 results
   b. Serial Dilution Series "D" as follows:
   (i) 1:10 dilution for CEA using Saline
      A. 90 µL of specimen to 810 µL of Saline
         1. Prepared 3 aliquots (A, B & C) at 200 ul.
         2. 1 Dilution/3 aliquots→3 results (ii) 1:40 dilution using Saline & remaining volume from 1:10 dilution in Saline
    A. 150 μL of 1:10 in Saline to 450 μL of Saline
        1. Prepared 3 aliquots (A, B & C) at 200 μL
        2. 1 Serial Dilution/3 aliquots→3 results
  NOTE: 1:40 not required for this validation 8. Testing was completed as defined by SOPs for the neat re-tests for CEA & Amylase testing, as well as the 1:10 dilutions in UD and Saline for CEA testing. All testing was performed on the same day.

9. All specimen aliquots, both NEAT and diluted, were stored at 4° C. after testing was completed.

Linearity and Accuracy

Intraclass Correlation (ICC), concordance correlation (CC), and bias were used to measure the agreement between CEA values obtained on neat pancreatic fluid specimens versus diluted pancreatic fluid specimens (both old and new dilution methods). See FIGS. 5 and 6.

The concordance for the old and new dilution method compared to neat (undiluted) CEA values were determine when data was analyzed in clinically relevant categories. The categories were defined by using 192 ng/mL as the cut-off between Low CEA and High CEA. A CEA value of 192 ng/mL was selected, because this value has been used to discriminate between mucinous and non-mucinous cysts. Values at or above 192 ng/mL indicate mucinous cysts; values below this cut-off indicate non-mucinous cysts. The concordance with neat CEA values was improved using the New CEA method as compared to the Old CEA method (Table 2).

TABLE 2

Concordance between neat CEA values and diluted CEA values (Old vs. New Method) when data was analyzed in high (>192 ng/mL) and low (<192 ng/mL) CEA categories.

| Neat CEA values compared to: | % Concordance |
| --- | --- |
| Old method | 88.04% |
| New Method | 91.30% |

Sensitivity and Specificity

The sensitivity and specificity for measuring the CEA analyte is described by the manufactures of the Elecsys 2010 CEA analyzer (Roche, REF 11731629, http://www.roche.com.mx/fmfiles/re7143001/ElecsysCEA.pdf). The range in which CEA can be measured by this instrument is 0.200-1000 ng/mL, with 0.200 being the lower limit of detection. Any interfering substances present in pancreatic cyst fluid will be less abundant when dilution in saline occurs.

Precision

Coefficient of variation (CV) was used to assess the reproducibility of CEA values obtained on neat pancreatic fluid specimens versus diluted pancreatic fluid specimens (both old and new dilution methods). Please see Table 3 for the inter-run and intra-run reproducibility of old dilution method and Table 4 for inter-run and intra-run reproducibility of new dilution method.

TABLE 3

Inter-Run & Intra-Run Reproducibility-Old CEA Dilution Method

| Overall Inter Run MEAN CV | 4.16% | Overall Intra Run MEAN CV | 2.85% |
| --- | --- | --- | --- |
| Overall Inter Run Median CV | 4.00% | Overall Intra Run Median CV | 2.16% |

TABLE 4

Inter-Run Reproducibility-New CEA Dilution Method

| Overall Inter Run MEAN CV | 4.72% | Overall Intra Run MEAN CV | 2.50% |
| --- | --- | --- | --- |
| Overall Inter Run Median CV | 4.67% | Overall Intra Run Median CV | 2.03% |

Validation Conclusions

Linearity & Accuracy

There is an increase in agreement between the neat CEA value and the diluted CEA value using the New CEA Dilution method versus the Old CEA dilution method. Intraclass Correlation (ICC), concordance correlation (CC), bias, and categorical concordance between diluted and neat CEA values were all improved using the New CEA dilution method as compared to the Old CEA dilution method.

Sensitivity & Specificity

Sensitivity and Specificity are per the manufacturer's description for the Elecsys 2010 (Roche) instrument CEA analyzer.

Precision

Both methods showed good reproducibility, with the New CEA Dilution method showing a slight improvement in overall intra-run reproducibility. Inter-run reproducibility is generally accepted with CVs of less than 15%; intra-run reproducibility is generally accepted with CVs of less than 10%. All CVs for the New CEA dilution method were less than these values.

The results described above, indicate that the New CEA Dilution method performance is similar to or improved compared to the current clinical method (i.e. Old CEA Dilution method) for pancreatic fluid samples. Therefore the New CEA Dilution method is acceptable for implementation on clinical pancreatic fluid specimens received for CEA testing.

REFERENCES

1. Clinical Chemistry 2010; 56; 1351-1352
2. Gastroenterol 2004; 126: 1330-1336
3. AM J Gastroenterol 2007; 102:2339-2349
4. http://www.salimetrics.com/documents/spit-tips/publications/Inter%20and%20Intra%20Assay%20Coefficients%20-of%20Variability.pdf The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges, which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed:

1. A method of measuring carcinoembryonic antigen in a biological sample, the method comprising:
   diluting the biological sample with a diluent at a ratio of biological sample to diluent of about 1:10 to about 1:50 to form a diluted biological sample;
   measuring the amylase level of the diluted biological sample; and
   measuring carcinoembryonic antigen level in the diluted biological sample,
   wherein the measured carcinoembryonic antigen amount is not adjusted with a correction factor.

2. The method of claim 1, wherein the diluent is saline, Diluent Universal, or a combination thereof.

3. The method of claim 1, wherein the biological sample is undiluted prior to the diluting step.

4. The method of claim 1, wherein diluting the biological sample with a diluent comprises diluting the biological sample with a diluent in a ratio of about 1:10.

5. The method of claim 1, wherein diluting the biological sample with a diluent comprises diluting the biological sample with a diluent in a ratio of about 1:40.

6. The method of claim 1, wherein the biological sample is not present in sufficient volume to accurately measure carcinoembryonic antigen level prior to the diluting step.

7. The method of claim 1, wherein the biological sample has a high viscosity prior to the diluting step.

8. The method of claim 7, wherein the high viscosity is due to the presence of mucin in the biological sample.

9. The method of claim 1, wherein the carcinoembryonic antigen levels in the biological sample exceed the measurement capabilities of an instrument being used to measure carcinoembryonic antigen level prior to the diluting step.

10. The method of claim 1, wherein the biological sample is selected from pancreatic fluid, pancreatic cyst fluid and combinations thereof.

* * * * *